United States Patent [19]

Klueppel et al.

[11] Patent Number: 5,182,100
[45] Date of Patent: Jan. 26, 1993

[54] PLAQUE-INHIBITING ORAL AND DENTAL CARE PREPARATIONS

[75] Inventors: Hans-Juregen Klueppel, Duesseldorf; Bernd Fabry, Korschenbroich, both of Fed. Rep. of Germany

[73] Assignee: Henkel Kommandigesellschaft auf Aktien, Duesseldorf-Holthausen, Fed. Rep. of Germany

[21] Appl. No.: 829,085

[22] PCT Filed: Aug. 7, 1990

[86] PCT No.: PCT/EP90/01290

§ 371 Date: Feb. 14, 1992

§ 102(e) Date: Feb. 14, 1992

[87] PCT Pub. No.: WO91/02510

PCT Pub. Date: Mar. 7, 1991

[30] Foreign Application Priority Data

Aug. 16, 1989 [DE] Fed. Rep. of Germany ....... 3927011

[51] Int. Cl.⁵ ................................................. A61K 7/16
[52] U.S. Cl. ......................................... 424/49; 424/56; 424/57
[58] Field of Search ................................. 424/49–58

[56] References Cited

U.S. PATENT DOCUMENTS

3,963,832 6/1976 Hashimoto et al. ............... 424/56
4,956,116 9/1990 Fabry et al. .................... 252/174.16
5,041,597 8/1991 Fabry et al. .......................... 558/177

FOREIGN PATENT DOCUMENTS

338191 10/1989 European Pat. Off. .
3802815 8/1989 Fed. Rep. of Germany .
3812718 10/1989 Fed. Rep. of Germany .
3927011 2/1991 Fed. Rep. of Germany .
9102510 3/1991 PCT Int'l Appl. .

*Primary Examiner*—Shep K. Rose
*Attorney, Agent, or Firm*—Ernest G. Szoke; Wayne C. Jaeschke; Norvell E. Wisdom, Jr.

[57] ABSTRACT

Described are mouth and dental care preparations with improved action against the formation of plaque and containing as their active ingredients sulfophosphoric acid salts of the formula (I):

$$R^1-O-\underset{\underset{OR^2}{|}}{\overset{\overset{O}{\|}}{P}}-(OC_nH_{2n})_x-O-R^3-SO_3^{(-)}M^{(+)}$$

in which $R^1$ and $R^2$, independently of each other, are hydrogen, or the cation $M^{(+)}$ and $R^2$ together form the group $$(OC_nH_{2n})_x-O-R^3-SO_3^{(-)}M^{(+)},$$

$R^3$ is an alkylene, hydroxyalkylene or alkenylene group with 8–22 C-atoms, n=2 or 3, x=0 or a number between 1 and 30 and $M^{(+)}$ is an alkali metal ion, the ammonium ion or a mono-, di- or trialkanolammonium ion with 2–4 C-atoms in the alkanol group. The preparations inhibit in vitro the dissolution and crystal growth of hydroxyapatite.

6 Claims, No Drawings

PLAQUE-INHIBITING ORAL AND DENTAL CARE PREPARATIONS

BACKGROUND OF THE INVENTION

1. Field of the Invention

This invention relates to the use of sulfophosphoric acid ester salts as plaque-inhibiting agents in oral and dental care preparations having an improved antiplaque effect.

2. Statement of Related Art

Oral and dental care preparations are products which are used to clean and care for the teeth, the oral cavity and the throat. In addition to eliminating halitosis and tooth coatings, their function is to prevent diseases of the teeth and gums, particularly caries and parodontosis. A prerequisite in this regard generally recognized among experts is protection of the dental enamel against demineralization and inhibition of plaque formation.

It is known that water-soluble organic phosphates are effective to a certain extent in reducing the solubility of apatite and the crystal growth of hydroxyl apatite. However, the compounds are not surface-active. Surface-active compounds of the type used to improve the cleaning effect of oral and dental care preparations, for example sodium lauryl sulfate, do not have a favorable effect in reducing the demineralization of dental enamel or in inhibiting plaque formation.

Surface-active sulfophosphoric acid alkenyl ester salts are known as surfactants having good performance properties, for example high foam stability in hard water, high alkali stability and good wetting power, cf. for example DE-OS 38 02 815. These products are prepared by sulfonation of phosphoric acid mono- and/or diesters of unsaturated fatty alcohols and neutralization with alkali metal hydroxide, ammonia or alkanolamines. German patent application P 38 12 718.0 also describes saturated sulfophosphoric acid alkyl ester salts which may be obtained by sulfonation of phosphoric acid mono- and/or diesters of saturated fatty alcohols with sulfur trioxide and neutralization of the sulfonates with alkali metal hydroxide, ammonia or alkanolamines. Adducts of 1 to 30 mol ethylene oxide with unsaturated or saturated fatty alcohols can also be similarly converted into phosphoric acid mono- and/or diesters and sulfonated.

DESCRIPTION OF THE INVENTION

Summary of the Invention

It has now surprisingly been found that these sulfophosphoric acid ester salts not only have good surface-active properties, they are also highly compatible with mucous membrane and reduce the solubility of hydroxyl apatite and inhibit the growth of hydroxyl apatite crystals under in vitro conditions. Accordingly, there is every prospect that these compounds will prevent the demineralization of dental enamel and counteract the formation of plaque.

The present invention relates to the use of surface-active sulfophosphoric acid ester salts corresponding to general formula I

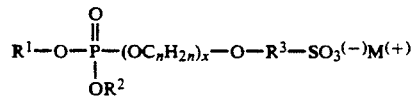

in which $R^1$ and $R^2$ independently of one another represent hydrogen or a cation $M^{(+)}$, in addition to which $R^2$ may also be a group $(OC_nH_{2n})_x$—O—$R^3$—$SO_3^{(-)}M^{(+)}$, $R^3$ is an alkylene, hydroxyalkylene or alkenylene group containing 8 to 22 carbon atoms, $n=2$ or 3, $x=0$ or a number of 1 to 30 and $M^{(+)}$ is an alkali metal, ammonium, mono-, di- or trialkanolammonium ion containing 2 to 4 carbon atoms in the alkanol group, as plaque-inhibiting agents in the production of oral and dental care preparations.

DESCRIPTION OF PREFERRED EMBODIMENTS

Surface-active sulfophosphoric acid ester salts corresponding to formula I and processes for their production are known from the publications cited above. Compounds corresponding to formula I in which $R^3$ is a $C_{8-22}$ alkylene or hydroxyalkylene group and mixtures of such compounds are obtained by the process described in DE-OS 38 02 815. Compounds corresponding to general formula I in which $R^3$ is a (saturated) $C_{8-22}$ alkylene group are obtained by the process described in German patent application P 38 12 718.0. The —$SO_3$—H— group is preferably situated at a carbon atom which is directly connected to other carbon atoms (so-called secondary carbon atom).

The oral and dental care preparations according to the invention preferably contain sulfophosphoric acid ester salts corresponding to formula I in which $R^3$ is a hydroxyalkylene or alkenylene group containing 18 carbon atoms and $x=0$. Compounds such as these corresponding to formula I are obtained from mono- and dioleyl phosphate and mixtures of these phosphoric acid esters by sulfonation with sulfur trioxide and neutralization of the sulfophosphoric acid esters, for example with sodium or potassium hydroxide, ammonia, mono-, di- or triethanolamine or isopropanolamine.

In order adequately to remineralized dental enamel and develop their plaque inhibiting effect, the compounds corresponding to general formula I should be present in an adequate concentration. Accordingly, the present invention relates to oral and dental care preparations having an improved effect against the formation of plaque and for the prophylaxis of caries, characterized in that they contain a surface-active sulfophosphoric acid ester salt corresponding to general formula I in claim 1 in a quantity of 0.1 to 10% by weight in an aqueous or aqueous-alcoholic carrier.

The oral and dental care preparations according to the invention containing surface-active sulfophosphoric acid ester salts may be prepared in the various forms typical of such products, for example as mouthwashes, toothpastes or tooth powders.

In addition to the surface-active sulfophosphoric acid ester salts, the oral and dental care preparations according to the invention may contain the carriers and additives typical of the particular formulation.

Toothpastes or tooth creams are generally gel-form or paste-form preparations of water, thickeners, humectants, abrasives or polishes, surfactants, sweeteners, flavorings, deodorizing agents and agents against diseases affecting the mouth and teeth. The toothpastes according to the invention may contain typical polishes, including for example chalk, dicalcium phosphate, insoluble sodium metaphosphate, aluminium silicates, calcium pyrophosphate, fine-particle synthetic resins, silicas, aluminium oxide and aluminium oxide trihydrate.

Particularly suitable polishes for the toothpastes according to the invention are, above all, fine-particles xerogel silicas, hydrogel silicas, precipitated silicas, aluminium oxide trihydrate and fine-particle α-aluminium oxide or mixtures of these polishes in quantities of 15 to 40% by weight, based on the toothpaste as a whole. Suitable humectants are predominantly low molecular weight polyethylene glycols, glycerol, sorbitol or mixtures of these products in quantities of up to 50% by weight. Among the known thickeners, the thickening fine-particle gel silicas and hydrocolloids, such as for example carboxymethyl cellulose, hydroxyethyl cellulose, hydroxypropyl guar, hydroxyethyl starch, polyvinyl pyrrolidone, high molecular weight polyethylene glycol, vegetable gums, such as tragacanth, agar agar, carrageen moss, gum arabic, xanthan gum, and carboxyvinyl polymers (for example Carbopol ® types), are suitable. In addition to the surface-active sulfophosphoric acid ester salts, the oral and dental care preparations according to the invention may contain other surface-active substances, preferably anionic high-foaming surfactants, such as for example linear sodium alkyl sulfates containing 12 to 18 carbon atoms in the alkyl group, sodium salts of alkyl polyglycol ether sulfates containing 12 to 16 carbon atoms in the linear alkyl group and 2 to 6 glycol ether groups in the molecule, of alkyl-($C_{12-16}$)-benzenesulfonate, linear alkane-($C_{12-18}$)-sulfonates, sulfosuccinic acid monoalkyl-($C_{12-18}$)-esters, sulfated fatty acid monoglycerides, sulfated fatty acid alkanolamides, sulfoacetic acid alkyl-($C_{12-18}$)-esters, acyl sarcosides, acyl taurides and acyl isethionates containing 8 to 18 carbon atoms in the acyl group. Nonionic surfactants, for example ethoxylates of fatty acid mono- and diglycerides, fatty acid sorbitan esters and ethylene oxide/propylene oxide block polymers, are also suitable. However, the sulfophosphoric acid ester salts are preferably the only surfactants in the toothpastes according to the invention. Other typical toothpaste additives are:

preservatives and antimicrobial agents, such as for example p-hydroxybenzoic acid methyl, ethyl or propyl ester, sodium sorbate, sodium benzoate, bromochlorophene, phenyl salicylic acid ester, thymol, etc.

anti-plaque agents, for example organophosphonates, such as 1-hydroxyethane-1,1-diphosphonic acid, 1-phosphonopropane-1,2,3-tricarboxylic acid and others which are known, for example, from U.S. Pat. No. 3,488,419, DE-OS 22 24 430 and DE-OS 23 43 196, other caries-inhibiting agents, such as for example sodium fluoride, sodium monofluorophosphate, tin fluoride, sweeteners, such as for example saccharin sodium, sodium cyclamate, sucrose, lactose, maltose, fructose or Aspartame ® (L-aspartyl-L-phenylalanine methyl ester), flavorings, such as for example peppermint oil, spearmint oil, eucalyptus oil, aniseed oil, fennel oil, caraway oil, menthyl acetate, cinnamic aldehyde, anethol, vanillin, thymol and mixtures of these and other natural and synthetic flavorings, pigments, such as titanium dioxide for example, dyes, buffers, such as for example primary, secondary or tertiary alkali metal phosphates or citric acid/sodium citrate, wound-healing and anti-inflammatory agents, such as for example allantoin, urea, azulene, camomile-based agents and acetyl salicylic acid derivatives.

One preferred embodiment of the invention is a toothpaste in the form of an aqueous paste-form dispersion containing polishes, humectants, viscosity regulators, flavoring oils and, optionally, other typical toothpaste components, characterized in that it contains a phosphoric acid ester salt corresponding to general formula I in a quantity of 0.5 to 10% by weight as the plaque-inhibiting agent.

Mouthwashes may readily contain a combination of aqueous alcoholic solutions varying in strength of ethereal oils, emulsifiers, astringent and toning drug extracts, plaque-inhibiting antibacterial additives and flavor correctants. One preferred embodiment of the invention is a mouthwash in the form of an aqueous or aqueous alcoholic solution containing typical flavoring oils, characterized in that it contains a sulfophosphoric acid ester salt corresponding to general formula I in a quantity of 0.01 to 5% by weight as the anti-plaque agent.

In mouthwashes which are diluted before use, adequate effects can be obtained with higher concentrations corresponding to the intended dilution ratio. The following Examples are intended to illustrate the invention without limiting it in any way.

EXAMPLES

1. Determination of the reduction of apatite solubility (ASR)

1.1 Blank test 0.5 g hydroxyl apatite powder (specific surface 60 $m^2/g$, Merck) was introduced into a reaction vessel containing 300 ml deionized water thermostatically controlled to 37° C. The pH value of the suspension was kept constant at pH 5 by means of an automatic burette with which lactic acid solution can be added. The quantity of 0.1 molar lactic acid solution used for pH stabilization was recorded by a recorder. The consumption of lactic acid recorded after 2 hours corresponded to the solubility of the untreated hydroxyl apatite (Su).

1.2 Measurement

The measurement was carried out as in 1.1. Quantities of 30 mg and 150 mg (solids) of the active substance to be tested were dissolved before addition of the hydroxyl apatite powder. The consumption of lactic acid recorded after 2 hours corresponded to the solubility of the treated apatite powder (St).

The reduction in apatite solubility by the active substance is calculated in accordance with the following equation:

$$ASR\ [\%] = \frac{(Su - St)\ 100\ [\%]}{Su}$$

The results of the measurements (ASR) are shown in Table I.

2. Determination of the inhibition of crystal growth of hydroxyl apatite (CGI)

2.1 Blank test 400 ml of a 0.0008 molar solution of $KH_2PO_4$ and 45 ml of a 0.012 molar solution of $CaCl_2$ were introduced into a reaction vessel. This solution was adjusted to a pH value of 7.4 by titration with a 0.05 molar solution of KOH. After the pH value had remained stable for at least 30 minutes, 100 mg hydroxyl apatite powder (specific surface 60 m²/g, Merck) were added. The pH value of the suspension was kept constant at pH 7.4 by means of an automatic burette with which 0.05 molar KOH solution can be added. The quantity of 0.05 molar KOH solution used for pH stabilization was recorded by a recorder. The consumption of KOH solution recorded after 2 hours (Ku) corresponded to the formation of hydroxyl apatite (growth of the crystals of the suspension).

2.2 Measurement

The measurement was carried out as in 2.1. Before adjustment of the pH value, quantities of 6 mg and 30 mg (solids) of the active substance to be tested were dissolved.

The consumption of 0.05 molar KOH solution (Kb) recorded after 2 hours corresponded to the formation of hydroxyl apatite (growth of the crystals in the suspension) under the effect of the active substance.

The inhibition of crystal growth by the active substance is calculated in accordance with the following equation:

$$CGI\,[\%] = \frac{(K_u - K_b)\,100\,[\%]}{K_u}$$

The results of the measurements (CGI) are shown in Table I.

3. Active substances according to the invention

The sodium salts of sulfonated oleyl phosphates were used as the active substances to be used in accordance with the invention. The products used had been produced from technical oleyl alcohol qualities by the process described in DE-OS 38 02 815:

3.1 Oleyl (iodine value 89) phosphate sulfonate Na salt

The product was prepared in accordance with DE-OS 38 02 815, Example 1.1 (phosphation) and 2.1 (sulfonation). The oleyl phosphate had been prepared from a technical oleyl alcohol containing small amounts of cetyl alcohol and having an iodine value of 89 and a hydroxyl value of 205 (HD-Ocenol ® 80/85). The oleyl phosphate contained 43.3% by weight monoester, 38.4% by weight diester and, as secondary products, 3.4% by weight triester and 13.0% by weight unreacted oleyl alcohol.

The sulfonate contained 16% by weight anionic surfactant (0.3 mval/g) and 82% by weight water.

3.2 Oleyl (iodine value 95) phosphate sulfonate, Na salt

The product was prepared by the same process from an HD-Ocenol ® 92-96 (iodine value 95, hydroxyl value 208). The oleyl phosphate (intermediate product) contained 63.6% by weight monoester, 26.2% by weight diester, 4.9% by weight triester and 15.1% by weight unreacted oleyl alcohol. 3.3 Oleyl (iodine value 108) phosphate sulfonate, Na salt The product was prepared by the same process from a mixture of oleyl and linoleyl alcohol (from rapeseed oil, iodine value 108, hydroxyl value 205). The oleyl linoleyl phosphate (intermediate product) contained 41.1% by weight monoester, 42.9% by weight diester, 3.2% by weight triester and 12.8% by weight unreacted oleyl linoleyl alcohol.

4. A surfactant typically used in oral and dental care preparations, namely sodium lauryl sulfate, was used for comparison.

TABLE I

| Test substance | ASR | | CGI | |
|---|---|---|---|---|
| | 30 mg | 150 mg | 6 mg | 30 mg |
| 3.1 | 11% | 46% | 19% | 56% |
| 3.2 | 18% | 74% | 22% | 60% |
| 3.3 | 21% | 56% | 17% | 55% |
| 4. Na lauryl sulfate | 0 | 0 | 0 | 0 |

5. Application Examples 5.1 Toothpaste

| | |
|---|---|
| Precipitated silica[1] | 18% by weight |
| Thickening silica (pyrogenic)[2] | 0.8% by weight |
| Oleyl (iodine value 95) phosphate sulfonate, Na salt (acc. to Example 3.1) | 1.0% by weight |
| Sorbitol | 17.5% by weight |
| Glycerol | 17.5% by weight |
| Carboxymethyl cellulose[3] | 0.9% by weight |
| Sodium lauryl sulfate[4] | 2.0% by weight |
| Sodium fluoride | 0.22% by weight |
| Saccharin sodium | 0.2% by weight |
| Flavoring oils | 1.0% by weight |
| Water, preservative | ad 100% by weight |

5.2 Mouthwash

| | |
|---|---|
| Ethyl alcohol (96% by vol.) | 10% by weight |
| Polyoxyethylene sorbitan monolaurate[5] | 0.4% by weight |
| Flavoring oil | 0.3% by weight |
| Sorbitol (70% aqueous solution) | 8.0% by weight |
| p-Hydroxybenzoic acid methyl ester | 0.16% by weight |
| Oleyl (iodine value 95) phosphate sulfonate, Na Salt (acc. to Example 3.2) | 0.1% by weight |
| Water, dyes | ad 100% by weight |

[1] Sident ® 12 DS, a product of Degussa
[2] Aerosil ® 200, a product of Degussa
[3] Relatin ® 100 S8, a product of Henkel KGaA
[4] Texapon ® K1296, a product of Henkel KGaA
[5] Tween ® 29, a product of Atlas Chemie

What is claimed is:

1. An oral or dental care preparation, wherein the improvement comprises the presence in the preparation of a plaque-inhibiting effective amount of at least one surface-active sulfophosphoric acid ester salt corresponding to general formula I:

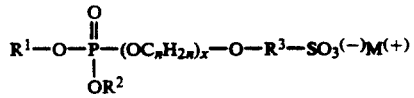

in which $R^1$ represents hydrogen or a cation $M^{(+)}$; $R^2$ represents hydrogen, a cation $M^{(+)}$, or a group $(OC_nH_{2n})_x$—O—$R^3$—$SO_3^{(-)}M^{(+)}$; $R^3$ is an alkylene, hydroxylakylene or alkenylene group containing 8 to 22 carbon atoms; n=2 or 3; x=0 or a number of 1 to 30; and $M^{(+)}$ is an alkali metal, ammonium, mono-, di- or trialkaneolammonium ion containing 2 to 4 carbon atoms in the alkanol groups.

2. An oral or dental care preparation as claimed in claim 1, wherein a surface-active sulfophosphoric acid ester salt corresponding to general formula I is used in a quantity of 0.1 to 10% by weight in an aqueous alcoholic carrier.

3. An oral or dental care preparation as claimed in claim 2, wherein $R^3$ in formula I is a hydroxyalkylene or alkenylene group containing 18 carbon atoms and x=0.

4. A dental care preparation as claimed in claim 1 that is a toothpaste in the form of an aqueous paste-like dispersion containing polishes, humectants, viscosity regulators, flavoring oils and, optionally, other typical toothpaste components, said toothpaste comprising a sulfophosphoric acid ester salt corresponding to general formula I in claim 1 in a quantity of 0.5 to 10% by weight as anti-plaque agent.

5. An oral care preparation as claimed in claim 1 that is a mouthwash in the form of an aqueous or aqueous-alcoholic solution containing typical flavoring oils, comprising a sulfophosphoric acid ester salt corresponding to general formula I in claim 1 in a quantity of 0.1 to 5% by weight as anti-plaque agent.

6. An oral or dental care preparation as claimed in claim 1, wherein $R^3$ in formula I is a hydroxyalkylene or alkenylene group containing 18 carbon atoms and $x=0$.

* * * * *